(12) United States Patent
Newman et al.

(10) Patent No.: US 10,476,142 B2
(45) Date of Patent: Nov. 12, 2019

(54) RADIO FREQUENCY ANTENNA WITH GRANULAR OR POWDER INSULATING MATERIAL AND METHOD OF MAKING THE SAME

(71) Applicant: CTS Corporation, Lisle, IL (US)

(72) Inventors: Robert L. Newman, Edwardsburg, MI (US); Douglas E. Cors, Elkhart, IN (US); James M. Post, Granger, IN (US)

(73) Assignee: CTS Corporation, Lisle, IL (US)

( * ) Notice: Subject to any disclaimer, the term of this patent is extended or adjusted under 35 U.S.C. 154(b) by 17 days.

(21) Appl. No.: 15/841,694

(22) Filed: Dec. 14, 2017

(65) Prior Publication Data

US 2018/0175488 A1    Jun. 21, 2018

Related U.S. Application Data

(60) Provisional application No. 62/437,133, filed on Dec. 21, 2016.

(51) Int. Cl.
*H01Q 1/32* (2006.01)
*H01Q 1/38* (2006.01)
(Continued)

(52) U.S. Cl.
CPC ......... *H01Q 1/3233* (2013.01); *G01N 27/221* (2013.01); *H01Q 1/3291* (2013.01);
(Continued)

(58) Field of Classification Search
CPC ..... H01Q 1/3266; H01Q 1/2208; H01Q 1/242
(Continued)

(56) References Cited

U.S. PATENT DOCUMENTS

| 3,701,086 A | 10/1972 | Sherman et al. |
| 3,943,470 A | 3/1976 | Bingham |

(Continued)

FOREIGN PATENT DOCUMENTS

| CN | 202759006 U | 2/2013 |
| EP | 1447819 A1 | 8/2004 |

(Continued)

OTHER PUBLICATIONS

M Feulner et al: 11 Microwave-Based Diesel Particulate Filler Monitoring—Soot Load Determination and Influencing Parameters, May 16, 2013 {May 16, 2013), DOI: 10.5162/sensor2013/P4.1 Retrieved from the Internet: URL:https://www.ama-science.org/proceedings/delails/1605.

(Continued)

*Primary Examiner* — Joseph J Lauture
(74) *Attorney, Agent, or Firm* — Daniel Deneufbourg

(57) ABSTRACT

A radio frequency antenna comprising an inner conductor or antenna surrounded by and spaced from an outer sleeve, the space between the inner conductor and the outer sleeve being filled with a granular or powder insulating material. A sealant material covers a first end of the outer sleeve for sealing and retaining the insulating material in the antenna. A method of making the antenna includes the step of bending the inner antenna and the outer sleeve during assembly following the steps of filling the space between the inner conductor and the outer sleeve with the insulating material and sealing the insulating material in the antenna. In one embodiment, the radio frequency antenna is adapted for transmitting and receiving radio frequency signals in a radio frequency vehicle exhaust control and sensor system.

15 Claims, 3 Drawing Sheets

(51) Int. Cl.
*G01N 27/22* (2006.01)
*H01Q 9/30* (2006.01)
*H01Q 1/22* (2006.01)
*H01Q 1/24* (2006.01)

(52) U.S. Cl.
CPC ............. *H01Q 1/38* (2013.01); *H01Q 9/30* (2013.01); *G01N 2027/222* (2013.01); *H01Q 1/2208* (2013.01); *H01Q 1/242* (2013.01); *H01Q 1/3266* (2013.01)

(58) Field of Classification Search
USPC .............................. 343/713, 895, 703, 702
See application file for complete search history.

(56) References Cited

U.S. PATENT DOCUMENTS

| | | | |
|---|---|---|---|
| 4,204,549 A | 5/1980 | Paglione | |
| 4,477,771 A | 10/1984 | Nagy et al. | |
| 4,764,233 A | 8/1988 | Ogihara et al. | |
| 4,841,988 A | 6/1989 | Fetter et al. | |
| 4,920,356 A | 4/1990 | Goebel et al. | |
| 4,945,318 A | 7/1990 | Kabachinski et al. | |
| 5,539,851 A | 7/1996 | Taylor et al. | |
| 6,123,567 A | 9/2000 | McCarthy | |
| 6,452,554 B1 | 9/2002 | Aoyama et al. | |
| 6,596,393 B1 | 7/2003 | Houston et al. | |
| 6,741,221 B2 | 5/2004 | Aisenbrey | |
| 6,953,619 B2 | 10/2005 | Dean et al. | |
| 7,194,383 B2 | 3/2007 | Clarke et al. | |
| 7,615,856 B2 | 11/2009 | Sakai et al. | |
| 8,201,746 B2 | 6/2012 | Guo et al. | |
| 8,384,396 B2 | 2/2013 | Bromberg et al. | |
| 8,384,397 B2 | 2/2013 | Bromberg et al. | |
| 8,665,160 B2 | 3/2014 | Uttermann et al. | |
| 8,692,719 B2 | 4/2014 | Yagi et al. | |
| 9,088,071 B2 | 7/2015 | Spencer et al. | |
| 9,159,019 B2 | 10/2015 | Takigahira | |
| 9,192,438 B2 * | 11/2015 | Thiel | A61B 90/57 |
| 9,196,958 B2 | 11/2015 | Arnold et al. | |
| 9,251,458 B2 | 2/2016 | Finn et al. | |
| 2003/0036369 A1 | 2/2003 | Buffmire et al. | |
| 2004/0217472 A1 | 11/2004 | Aisenbrey et al. | |
| 2006/0071874 A1 * | 4/2006 | Wither | H01Q 1/362 343/895 |
| 2008/0224922 A1 | 9/2008 | Cleland et al. | |
| 2011/0025581 A1 | 2/2011 | Geer et al. | |
| 2011/0050516 A1 | 3/2011 | Glabe et al. | |
| 2012/0062430 A1 * | 3/2012 | Nishijima | H01L 27/1225 343/703 |
| 2012/0162047 A1 | 6/2012 | Mizuno et al. | |
| 2015/0123688 A1 | 5/2015 | Sappok et al. | |
| 2017/0301630 A1 | 10/2017 | Nguyen et al. | |
| 2017/0324160 A1 | 11/2017 | Khoury | |

FOREIGN PATENT DOCUMENTS

| | | |
|---|---|---|
| GB | 516063 A | 12/1939 |
| JP | H06139836 A | 5/1994 |
| WO | 9200766 | 1/1992 |
| WO | 1993026013 | 12/1993 |
| WO | 2008056159 | 5/2008 |
| WO | 2009008525 A1 | 1/2009 |
| WO | 2011030703 A1 | 3/2011 |

OTHER PUBLICATIONS

John Hansson et al: 11A Method for Estimating Soot Load in a DPF Using an RF-based Sensor Examensarbete ulfort i Fordonssystem vid Tekniska hogskolan vid Linkopings universitet av, Jun. 11, 2012 {Jun. 11, 2012), KP055386001, Retrieved from the Internet: URL:hllps://pdfs.semanticscholar.org/269d/ [81 bbc993ed1f80c 7b86b368d6cflf580a38111.pdf.

* cited by examiner

RADIO FREQUENCY ANTENNA WITH GRANULAR OR POWDER INSULATING MATERIAL AND METHOD OF MAKING THE SAME

CROSS REFERENCE TO RELATED APPLICATION

This patent application claims priority and benefit of the filing date of U.S. Provisional Patent Application Ser. No. 62/437,133 filed on Dec. 21, 2016, the disclosure and contents of which is expressly incorporated herein in its entirety by reference.

FIELD OF THE INVENTION

This invention relates generally to a radio frequency antenna and, more specifically, to a radio frequency signal transmitting and/or receiving antenna assembly with a granular or powder interior insulating material.

BACKGROUND OF THE INVENTION

Radio frequency (RF)- and microwave-based sensing techniques, including cavity perturbation methods and the like, are used in many applications ranging from laboratory and research instrumentation to process control systems and even on-vehicle sensors. In many applications, antennas or probes are used to transmit and/or receive radio frequency or microwave signals to conduct these measurements.

Many conventional RF antennas are not robust and are incapable of surviving extended operation with exposure to high temperatures, high vibration levels, thermal shock, corrosive or dirty environments, oxidizing or reducing conditions, and the like. Environmental exposure, rain, snow, and salt water for example, as well as exposure to chemicals and solvents, such as oils, fuels, acids, and similar chemicals, is also detrimental to many conventional RF/microwave probes and antennas.

The RF antenna described herein may be used in a number of applications, ranging from cavities to transmission lines, and even in free space. One range of applications include systems which monitor changes in the dielectric properties of a material or a mixture of materials in order to deduce some information regarding the state of the system.

One specific example includes a class of radio-frequency measurement systems applied to monitor and sense vehicle exhaust emissions or the state of various vehicle emission control and sensor devices. Radio-frequency or microwave systems used to monitor the loading state of vehicle particulate filters, such as the amount of soot or ash accumulated in a diesel particulate filter, is one exemplary application. Another application includes the monitoring of various gaseous species, such as oxygen or oxides of nitrogen (among others), adsorbed onto various catalytic emission after treatment components, such as three-way catalytic converters, selective catalytic reduction systems, oxidation catalysts, or lean NOx traps, to name a few. In yet another embodiment, the monitored parameter may be a change in the dielectric properties of the material itself, such as the filter material in the case of a diesel particulate filter, in one example and the catalysts substrate, wash coat, or catalyst material in yet another example. Although after treatment filters and catalysts are described and are particularly challenging, any filter system or catalyst system can use the technology described herein.

The present invention is directed to an improved and lower cost radio frequency antenna or measurement probe, and method of making the same, with granular or powder insulating material and suitable for extended operation over a range of conditions, including exposure to high temperatures in excess of 900 degrees Celsius, vibration, mechanical stresses, water and other liquids, and the like in, for example, a radio frequency vehicle exhaust control or sensor system.

SUMMARY OF THE INVENTION

The present invention is generally directed to a radio frequency antenna comprising an inner conductor surrounded by and spaced from an outer ground sleeve, the space between the inner conductor and the outer ground sleeve being filled with a granular or powder insulating material.

In one embodiment, the granular or powder insulating material is aluminum oxide, silicon oxide, or magnesium oxide.

In one embodiment, the granular or powder insulating material is a ceramic material.

In one embodiment, a sealant material covers a distal end of the outer ground sleeve for sealing and retaining the granular or powder insulating material in the outer ground sleeve.

In one embodiment, a distal end of the outer ground sleeve is crimped to a coaxial cable.

In one embodiment, the radio frequency antenna is adapted for transmitting and receiving radio frequency signals in a radio frequency vehicle exhaust control and sensor system.

The present invention is also directed to a radio frequency antenna assembly adapted for use in radio frequency vehicle exhaust control and sensor system and comprising a coaxial cable including a coaxial conductor, a center antenna including a distal end coupled to a distal end of the coaxial conductor of the coaxial cable, an outer sleeve surrounding and spaced from the center antenna and defining a cavity between the center antenna and the outer sleeve, and a granular or powder insulating material filling the cavity between the center antenna and the outer sleeve.

In one embodiment, a first distal end of the outer sleeve is crimped to the coaxial cable.

In one embodiment, a glass seal material covers a second distal end of the outer sleeve for sealing and retaining the granular or powder insulating material in the cavity defined between the center antenna and the outer sleeve.

In one embodiment, the insulating material is aluminum oxide, silicon oxide, or magnesium oxide.

In one embodiment, the insulating material is a ceramic material.

The present invention is further directed to a method of making a radio frequency antenna assembly comprising the steps of providing a coaxial cable with a coaxial center conductor, providing a center antenna, coupling a distal end of the center antenna to a distal end of the coaxial center conductor, providing and sliding an outer sleeve over the center antenna into a relationship surrounding and spaced from the center antenna and defining a circumferential cavity between the outer sleeve and the center antenna, securing a first end of the outer sleeve to the coaxial cable, providing and filling the cavity defined between the center antenna and the outer sleeve with an insulating granular or powder material, providing a seal material and covering a second end of the outer sleeve with the seal material for sealing and retaining the insulating material in the outer sleeve, and bending the center antenna and the outer sleeve into a desired final shape.

In one embodiment, the method further comprises the steps of providing and coupling a mounting nut over the second distal end of the outer sleeve, and providing and coupling a ferrule to the second distal end of the outer sleeve.

In one embodiment, the method further comprises the step of providing an insulating material made of aluminum oxide, silicon oxide, or magnesium oxide.

In one embodiment, the method further comprises the step of providing an insulating material made of ceramic material.

Other advantages and features of the present invention will be more readily apparent from the following detailed description of the preferred embodiment of the invention, the accompanying drawings, and the appended claims.

BRIEF DESCRIPTION OF THE DRAWINGS

These and other features of the invention can best be understood by the description of the accompanying FIGS. as follows.

DESCRIPTION OF THE EMBODIMENT

Figure 1:
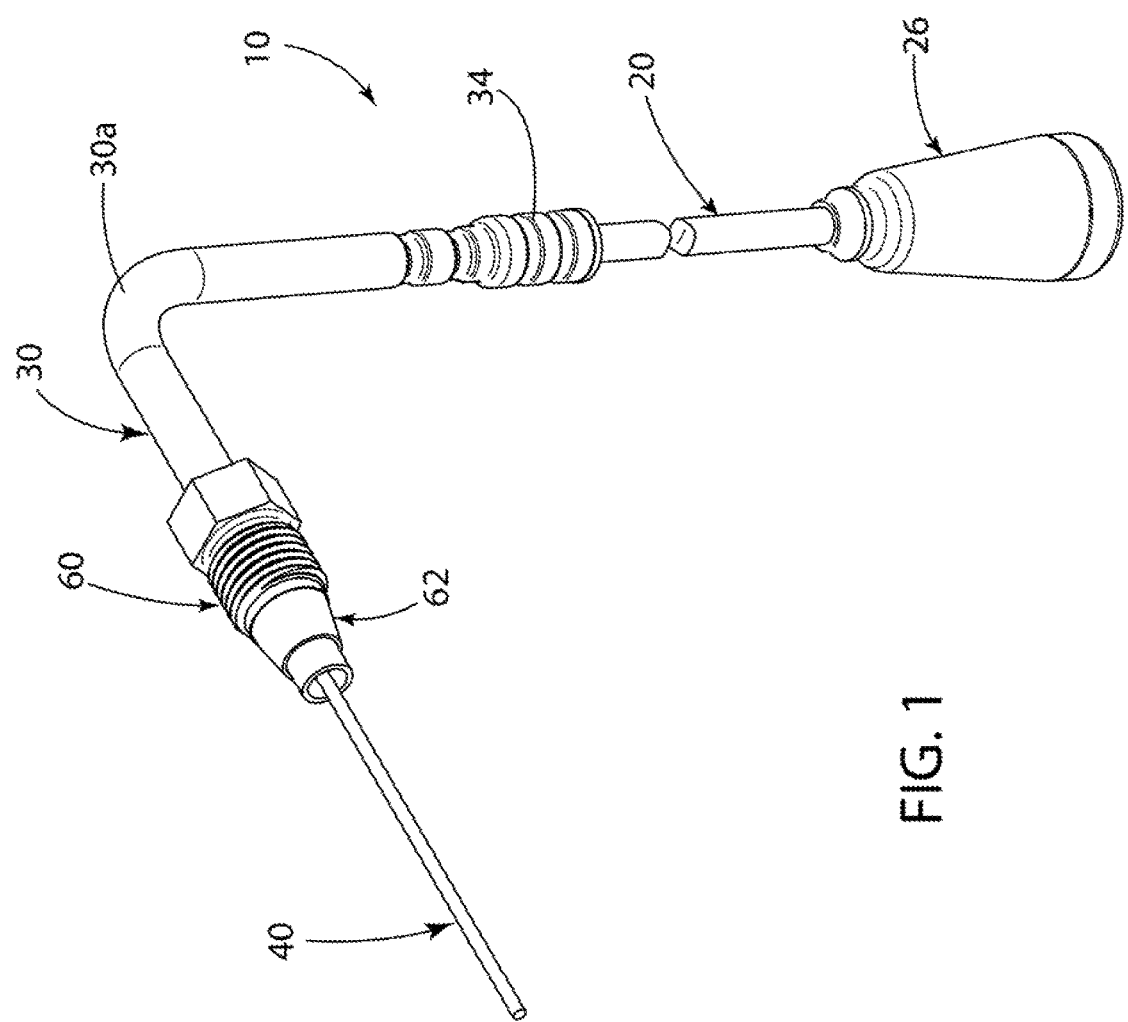
FIG. 1 is a broken perspective view of a radio frequency antenna assembly in accordance with the present invention.

FIG. 1 shows a radio frequency antenna/probe assembly 10 in accordance with the present invention which, in one embodiment, is a radio frequency antenna/probe assembly of the type generally designated by the numerals 224, 230, 242, and 246 in the radio frequency vehicle exhaust control system disclosed in U.S. Pat. No. 8,384,397 and US Published Patent Application No. US 2015/0123688 A1, the entire contents and disclosures of which are incorporated herein by reference as though fully set forth herein.

The antenna/probe assembly 10, which in one embodiment is adapted for transmitting and receiving radio frequency signals in an RF vehicle exhaust control and sensor system, comprises an elongate cylindrical coaxial cable 20 including an elongate coaxial center cylindrical conductor 22 having a first distal end welded to the distal end 44 of an elongate inner center rod antenna or conductor 40.

The distal end of the coaxial cable 20 opposite the distal end thereof with the conductor 22 welded to the center antenna 40 includes a connector 24 for connecting the antenna/probe assembly 10, and more specifically the coaxial center conductor 22 thereof, to a device suitable for transmitting and receiving radio frequency (RF) signals.

A protective cover or sleeve 26 surrounds the distal connector 24.

The antenna/probe assembly 10 further comprises an elongate outer ground tube or sleeve 30 surrounding and spaced from the center antenna 40 and the coaxial center conductor 22.

The space or gap between the exterior circumferential surface of the elongate center antenna 40 and the interior circumferential surface of the elongate outer tube or sleeve 30 defines an elongate interior circumferentially extending and generally donut shaped cavity 36.

In accordance with the present invention, the interior circumferential cavity or space or gap 36 between the outer sleeve 30 and the center antenna 40 is filled with an insulating material 50 which, in accordance with the present invention, comprises an insulating granular or powder material.

In accordance with the present invention, the use of a granular or powder insulating material allows for the material to advantageously flow freely and uniformly into and cover the entire area or space defining the interior sleeve cavity during assembly.

Figure 2:
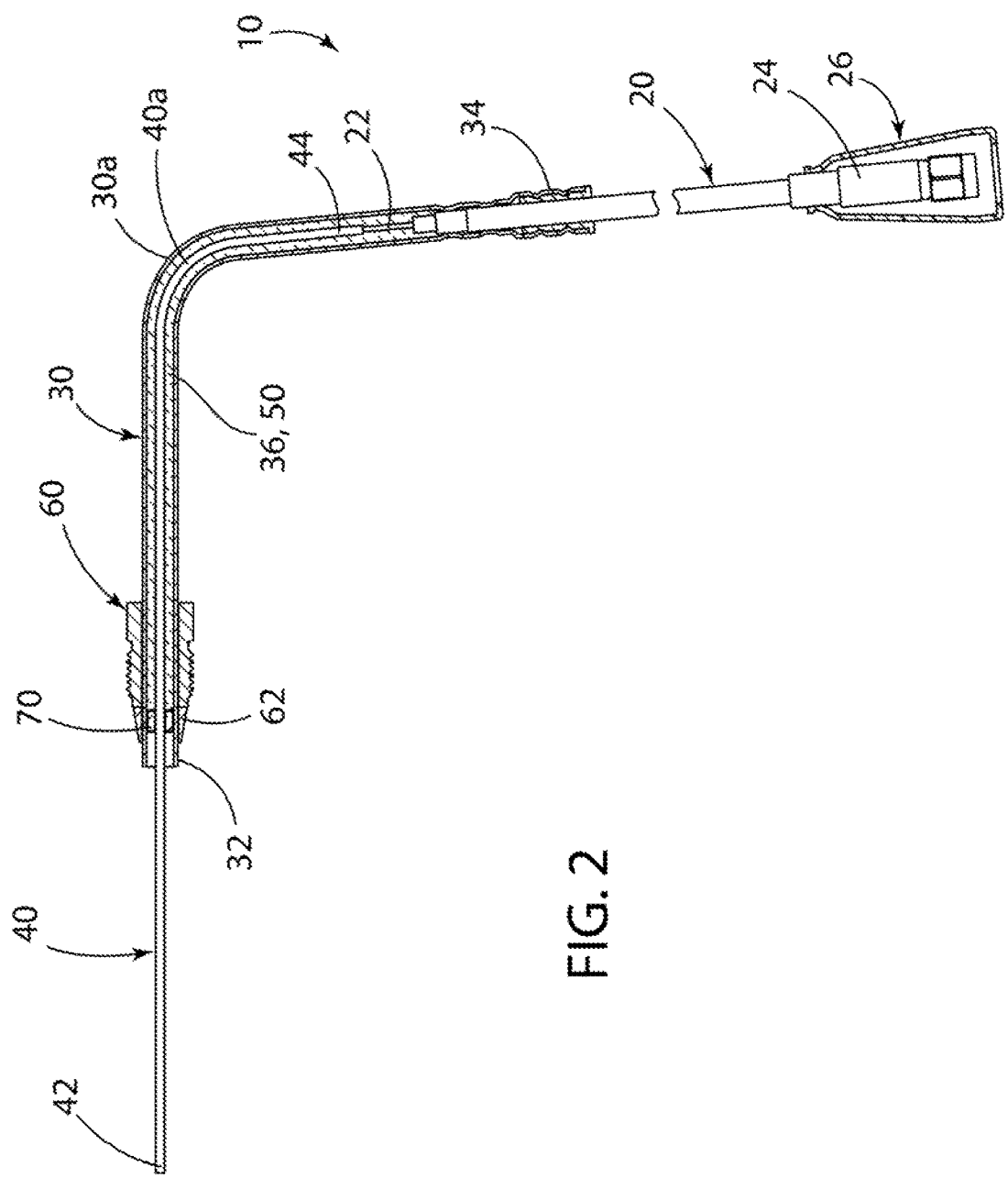
FIG. 2 is a broken vertical cross-sectional view of the radio frequency antenna assembly shown in FIG. 1.
Figure 3:
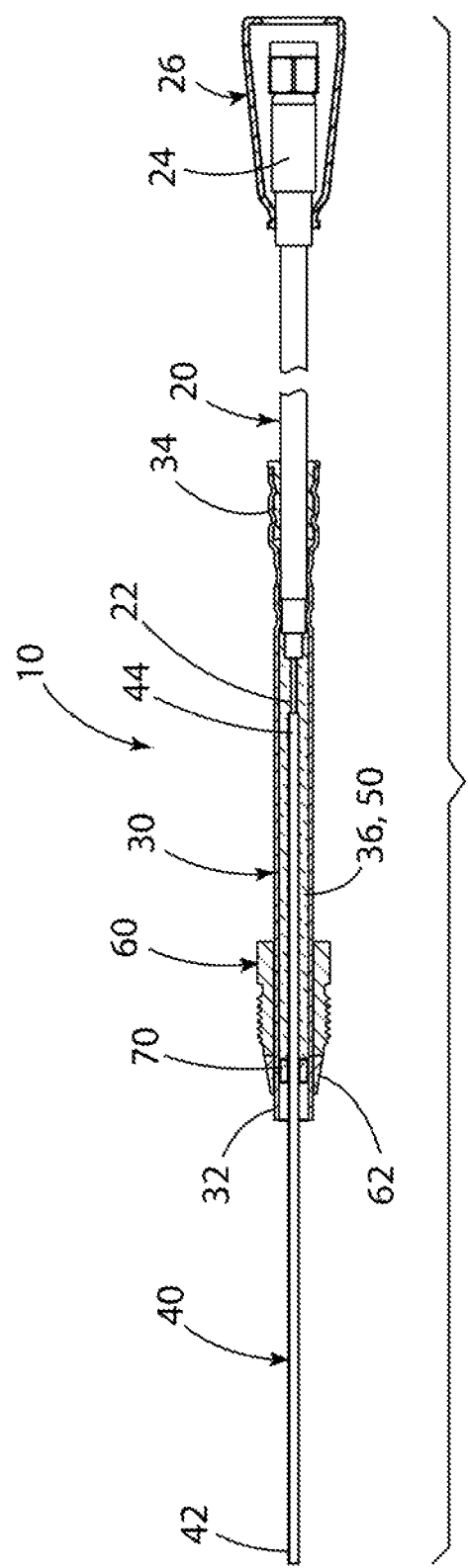
FIG. 3 is a broken vertical cross-sectional view of the radio frequency antenna assembly prior to bending and forming into its final L-shape as shown in FIG. 1.

In accordance with the present invention, the material 50 advantageously restricts movement of the center antenna 40 of the antenna/probe assembly 10 during use and further allows the antenna/probe assembly 10, and more specifically the outer sleeve 30 and the center antenna 40 thereof, to be bent at the same point during manufacturing from their respective straight positions as shown in FIG. 3 into their respective bent positions as shown in FIGS. 1 and 2 to define and form a generally L-shaped and bent antenna/probe assembly 10 as shown in FIGS. 1 and 2 that includes generally L-shaped curved bends 30a and 40a formed in, and located between the respective ends of, the outer sleeve 30 and the center antenna 40a respectively.

To meet temperature requirements during use in excess of nine hundred (900) degrees Celsius, the granular or powder material 50 may comprise for example aluminum oxide, silicon dioxide, magnesium oxide, or any other suitable dielectric material such as a ceramic material.

The material 50 fills the cavity 36 between a first distal end 32 of the outer sleeve 30 and the opposed distal end 34 thereof that is crimped to the coaxial cable 20.

The antenna/probe assembly 10 further comprises an elongate exterior tubular mounting nut 60 surrounding and abutting and rotatable relative to the exterior circumferential surface of the distal end 32 of the outer sleeve 30 and a tubular ferrule 62 abutting against a radial end face of the mounting nut 60 and also surrounding and abutting against the exterior circumferential surface of the distal end 32 of the outer sleeve 30.

A protective dielectric/ceramic/glass adhesive or sealant material 70 is located and fired in the interior of the distal end 32 of the outer sleeve 30 in a relationship abutting the interior circumferential surface of the outer sleeve 30 and surrounding and abutting the exterior circumferential surface of the center rod antenna 40 for plugging the distal end 32 of the outer sleeve 30 and retaining and sealing the material 50 in the interior of the antenna/probe assembly 10 and protecting the material 50 from exposure to contaminants during use.

In the embodiment shown, the distal end 42 of the center rod antenna 40 extends beyond the distal end 32 of the outer sleeve 30 of the antenna/probe assembly 10.

In accordance with the present invention, the method for manufacturing the antenna/probe assembly 10 of the present invention comprises at least the following steps: providing the coaxial cable 20 with the coaxial center conductor 22; providing the center antenna or conductor 40; welding the distal end 44 of the center antenna 40 to the distal end of the coaxial center conductor 22 of the coaxial cable 20; sliding the outer tube or sleeve 30 over the distal end 42 of the center antenna 40 opposite the end thereof welded to the coaxial center conductor 22 into a relationship with the outer tube or sleeve 30 surrounding and spaced from the center antenna 40 and the coaxial cable 20 with the first distal crimp end 34 of the outer sleeve 30 surrounding and covering the exterior surface of the coaxial cable 20 and the opposed distal end 32 of the outer sleeve 30 surrounding the exterior circumferential surface of the center antenna 40; crimping the crimp distal end 34 of the outer sleeve 30 to the exterior circumferential surface of the coaxial cable 20 thereby sealing and retaining the outer sleeve 30 on the coaxial cable 20 and defining a plug for retaining the insulating material 50 in the interior of the outer sleeve 30; filling the interior cavity 36 defined between the center antenna 40 and the outer tube or sleeve 30 with the insulating material 50 into a relationship in which the insulating material 50 extends and fills the space between the opposed ends 32 and 34 of the outer sleeve 30 and is retained therein by the glass seal material plug 70 at the end 32 thereof and the crimp plug at the opposed end 34 thereof; providing, applying, and firing the glass seal material 70 to and covering the opening defined in the radial end face of the distal end 32 of the outer sleeve 30 to seal the material 50 in the interior cavity 36; providing and installing the mounting nut 60 over the distal end 32 of the outer sleeve 30 into a relationship surrounding, abutting, and rotatable relative to the distal end 32 of the outer sleeve 30; providing and coupling the ferrule 62 to the antenna assembly 10 into a relationship abutting against the radial end face of the mounting nut 60 and the radial end face of the outer sleeve 30 and surrounding the fired glass seal 70; and then bending the center antenna 40 and the outer sleeve 30 from their respective straight positions as shown in FIG. 3 to their respective positions as shown in FIGS. 1 and 2 to form and define the generally L-shaped antenna/probe assembly 10 of the present invention.

Numerous variations and modifications of the radio frequency antenna and method of making the same described above may be effected without departing from the spirit and scope of the novel features of the invention. It is to be understood that no limitations with respect to the specific radio frequency antenna illustrated and method of manufacturing as described herein are intended or should be inferred. It is, of course, intended to cover by the appended claims all such modifications as fall within the scope of the claims.

What is claimed is:

1. A radio frequency antenna comprising a center antenna surrounded by and spaced from an outer ground sleeve, the space between the center antenna and the outer ground sleeve defining an interior cavity in the radio frequency antenna filled with a granular or powder insulating material wherein the granular or powder insulating material allows bending of the outer ground sleeve and the center antenna during manufacturing and restricts movement of the center antenna during use of the radio frequency antenna.

2. The radio frequency antenna of claim 1 wherein the granular or powder insulating material is aluminum oxide, silicon oxide, or magnesium oxide.

3. The radio frequency antenna of claim 1 wherein the granular or powder insulating material is a ceramic material.

4. The radio frequency antenna of claim 1 wherein a sealant material covers a distal end of the outer ground sleeve for sealing and retaining the granular or powder insulating material in the outer ground sleeve.

5. The radio frequency antenna of claim 1 wherein a distal end of the outer ground sleeve is crimped to a coaxial cable.

6. The radio frequency antenna of claim 1 adapted for transmitting and receiving radio frequency signals in a radio frequency vehicle exhaust control and sensor system.

7. A radio frequency antenna assembly adapted for use in radio frequency vehicle exhaust control and sensor system and comprising:
    a coaxial cable including a coaxial conductor;
    a center antenna including a distal end coupled to a distal end of the coaxial conductor of the coaxial cable;
    an outer sleeve surrounding and spaced from the center antenna and defining a cavity between the center antenna and the outer sleeve; and
    a granular or powder insulating material filling the cavity between the center antenna and the outer sleeve.

8. The radio frequency antenna assembly of claim 7 wherein a first distal end of the outer sleeve is crimped to the coaxial cable.

9. The radio frequency antenna assembly of claim 8 wherein a glass seal material covers a second distal end of the outer sleeve for sealing and retaining the granular or powder insulating material in the cavity defined between the center antenna and the outer sleeve.

10. The radio frequency antenna assembly of claim 7 wherein the granular or powder insulating material is aluminum oxide, silicon oxide, or magnesium oxide.

11. The radio frequency antenna assembly of claim 7 wherein the granular or powder insulating material is a ceramic material.

12. A method of making a radio frequency antenna assembly comprising the steps of:
    a) providing a coaxial cable with a coaxial center conductor;
    b) providing a center antenna;
    c) coupling a distal end of the center antenna to a distal end of the coaxial center conductor;
    d) providing and sliding an outer sleeve over the center antenna into a relationship surrounding and spaced from the center antenna and defining a circumferential cavity between the outer sleeve and the center antenna;
    e) securing a first end of the outer sleeve to the coaxial cable;
    f) providing and filling the cavity defined between the center antenna and the outer sleeve with an insulating granular or powder material;
    g) providing a seal material and covering a second end of the outer sleeve with the seal material for sealing and retaining the insulating material in the outer sleeve; and
    h) bending the center antenna and the outer sleeve into a desired final shape.

13. The method of claim 12 further comprising the steps of:
    a) providing and coupling a mounting nut over the second distal end of the outer sleeve;
    b) providing and coupling a ferrule to the second distal end of the outer sleeve.

14. The method of claim 12 further comprising the step of providing an insulating material made of aluminum oxide, silicon oxide, or magnesium oxide.

15. The method of claim 12 further comprising the step of providing an insulating material made of ceramic material.

* * * * *